(12) United States Patent
Schwarz

(10) Patent No.: US 7,983,470 B2
(45) Date of Patent: Jul. 19, 2011

(54) METHOD AND DEVICE FOR ASSESSING JOINS OF WORKPIECES

(75) Inventor: Joachim Schwarz, Kleinandelfingen (CH)

(73) Assignee: Precitec Vision GmbH & Co. KG, Eschborn (DE)

( * ) Notice: Subject to any disclaimer, the term of this patent is extended or adjusted under 35 U.S.C. 154(b) by 587 days.

(21) Appl. No.: 12/092,979

(22) PCT Filed: Nov. 10, 2006

(86) PCT No.: PCT/CH2006/000634
§ 371 (c)(1),
(2), (4) Date: May 19, 2008

(87) PCT Pub. No.: WO2007/053973
PCT Pub. Date: May 18, 2007

(65) Prior Publication Data
US 2008/0232677 A1    Sep. 25, 2008

(30) Foreign Application Priority Data
Nov. 14, 2005   (CH) ........................................ 1823/05

(51) Int. Cl.
*G06K 9/00*    (2006.01)
(52) U.S. Cl. ...................................................... 382/141

(58) Field of Classification Search .................. 382/108, 382/141, 145–152, 266; 348/68, 86, 87, 348/90, 92; 219/602, 612
See application file for complete search history.

(56) References Cited

U.S. PATENT DOCUMENTS

2005/0041852 A1 *   2/2005   Schwarz et al. .............. 382/152

FOREIGN PATENT DOCUMENTS

| DE | 43 12 241 A1 | 10/1994 |
| JP | 2000 271743 | 10/2000 |
| WO | 03/041902 A1 | 5/2003 |

OTHER PUBLICATIONS

International Search Report for PCT/CH2006/000634, Dated Jan. 4, 2007.
Photon Focus, User manual, Hurricane CameraLink Series, CMOS Area Scan Cameras, The Perfect Eye, Man021 Oct. 2005 V1.1.

* cited by examiner

*Primary Examiner* — Duy M Dang
(74) *Attorney, Agent, or Firm* — McCormick, Paulding & Huber LLP

(57) ABSTRACT

For assessing the position and quality of joins a combined image of a join including a light line image and a grey value image is taken in the same sensor, but in two different regions of the sensor. The grey value image is evaluated to detect the quality of the join. This allows both the position and the quality of the join to be detected in a simple way.

19 Claims, 2 Drawing Sheets

METHOD AND DEVICE FOR ASSESSING JOINS OF WORKPIECES

REFERENCE TO RELATED APPLICATIONS

This application claims the priority of Swiss Patent Application No. 1823/05 which was filed on 14 Nov. 2005 and the entire disclosure of which is incorporated herewith by reference.

BACKGROUND

The invention concerns a method for detecting a join location of workpieces wherein by means of a light line intersection method lines of light are photographed for capturing the three dimensional course of the join location and further a grey value image of the join location is taken, and wherein the grey value image is evaluated for assessing the quality of the join, with the lines of light for the light line intersection method and grey value image being photographed by one sensor, especially a CMOS sensor. The invention further concerns uses of this method as well as an apparatus for recognition of join locations.

STATE OF THE ART

It is known from WO 03/041902 to take a photograph of the join position and of a light line pattern to determine the position and quality of join locations. The thereby photographed grey value image is evaluated to determine the quality of the join location. This method achieves good results.

SUMMARY OF THE INVENTION

The invention has as its basic object the improvement of such a method.

This is achieved in a case of the previously mentioned method in that the photographing of the light line occurs in a first area of the sensor and a photographing of a grey value image occurs in a second area of the sensor different from the first area, which areas are time-wise differently exposed and which areas of the sensor are time-wise differently interrogated.

The division of the sensor and the time-wise different exposure and interrogation of the sensor makes possible a very fast triangulation evaluation in the first sensor area and thereby an almost gapless 3D-representation and evaluation of join locations, such as for example welding and adhesive beads. The combination of both grey image evaluation and fast triangulation achieved by separation of one sensor into two sensor regions with different interrogation frequencies achieves the possibility of working so fast with the light line intersection method that a fast 3D measurement of the join location can take place and additionally the recognition and evaluation of local fault spots by the grey image analysis is possible.

In a first preferred implementation of the invention an independent asynchronous reading out of the regions of the sensor occurs. Especially preferred is another implementation which includes a synchronous reading out into a memory from which data blocks are then read out for evaluation with each data block including at least one light line image, especially a complete light line image, and a portion of the grey value image.

The invention further lies in solving the basic object of making an approved apparatus.

This occurs by way of the initially mentioned apparatus for recognition of the join locations having a light line projecting unit, a photographing unit, as well as a light line and grey value image evaluation unit. The photographing unit is constructed to take one image which contains both light line and grey value images.

BRIEF DESCRIPTION OF THE DRAWINGS

In the following exemplary embodiments and special advantages of the invention are explained in more detail with the help of the drawings. The drawings are.

DESCRIPTION OF THE PREFERRED EMBODIMENTS

Figure 1:
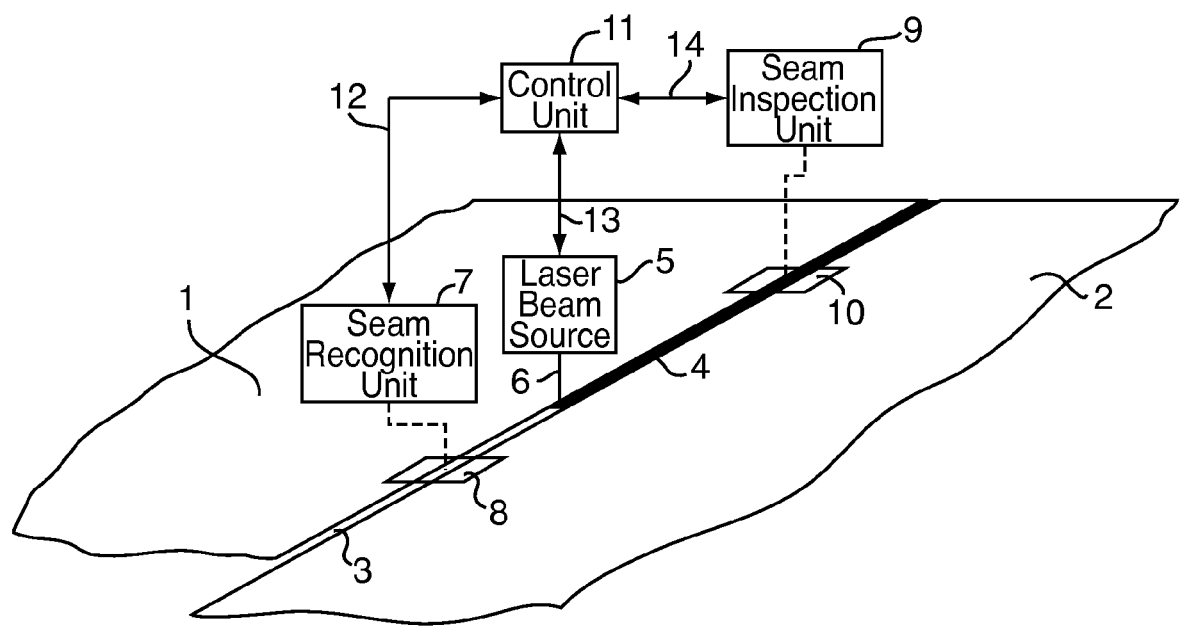
FIG. 1 a schematic view of a laser welding process for the welding of plates.
Figure 2:
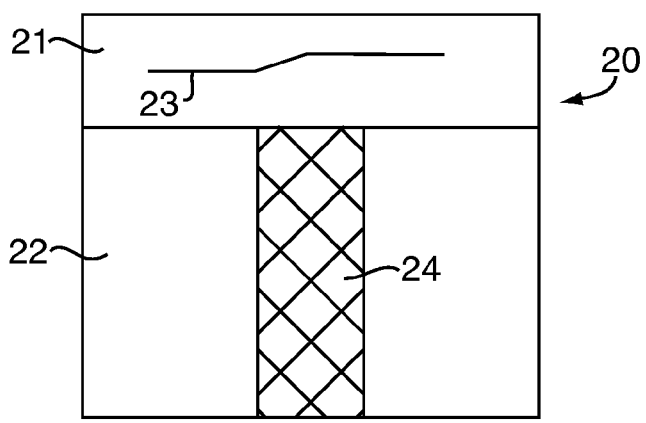
FIG. 2 a schematic view of a sensor having the two sensor areas of the invention.

FIG. 1 shows schematically the welding of a plate (or of a so-called tailored blank) made of pieces of sheet metal 1 and 2 which are buttingly pushed together along a join line 3. Usually planar pieces of differing thickness and/or differing characteristics are joined into one element, the plate (tailored blank). This element then often is later deformed into a construction component, for example, into a component for an automobile.

A laser beam 6 from a laser beam source 5 is moved along the join line 3 and welds the sheets 1 and 2 to one another and leaves behind it the welded seam 4. It is unimportant as to whether the laser beam source 5 is moved relative to stationary work pieces or if the workpieces are moved relative to a stationary laser. It is known to determine the position of the join line 3 by way of a seam recognizing unit 7 so that the laser bean source 5 and the beam 6 can exactly follow the course of the join line. For this, in a known way, the course of the join line 3 is determined by way of the light intersecting method as previously explained. According to this, the unit 7 contains, according to the state of the art as well as according to the invention, a device for creating at least one line of light, especially a laser light line, running essentially perpendicularly to the course of the join line 3. The course of the light line is captured by a camera to achieve a recognition of the join line. This is basically known and need not be explained in more detail here. The captured area is indicated at 8 in the figure, where it is not drawn to scale; and the captured area can for example can have a size of 8×8 mm or 10×10 mm. Further it is also known to take a grey value photograph in the region of the light line, to likewise recognize the course of the join line 3. The picture taken by the unit 7 is transmitted over a conductor 12 to an evaluation and control unit 11, which can also be separate units for evaluation and control, and accordingly the position of the laser beam is controlled to exactly pursue the join position 3.

For assessing the seam quality of the welded seam 4, following the welding in the present case on one hand the light line intersecting process according to WO 03/041902 is carried out to measure the geometric data, such for example convexity, concavity and mutual edge displacement. For this a seam inspecting unit 9 is provided. The region captured by this unit is indicated as region 10 in the figure and again is not drawn to scale and can for example be 8×8 mm or 10×10 mm in size. On the other hand, in the present case for the testing of the welded seam 4 according to WO 03/041902 a grey value photograph is also taken, with that grey value photograph being evaluated for recognition of the quality of the welded seam. The evaluation of the grey value image is to especially report localized faults such as porosities, small holes and failures of thorough welding. For this the unit 9 is equipped, on one hand, for the creation of at least one line of light extending perpendicularly to the welded seam 4. This light line is preferably created by a light line laser with high optical power (for example by 50 mW to 100 mW laser diodes on a small line) so that, taking into consideration existing differences in the reflectivity properties of the outer surfaces, sufficient light is reflected onto the sensor in the unit 9 to allow recognition of the light line. The sensor in the unit for the light line is therefore preferably a sensor 20 which as mentioned can be provided in the unit 9, with that sensor 20 having a first area 21 and a second area 22. In the first area an image 23 of a triangulation line is represented and in the second area the grey scale image 24 of the join line or welded seam 4 is represented. The images in the two areas are taken in controlled synchronism with the creation of the laser light lines or with the illumination for the grey value photograph so that each sensor 21, 22 receives its corresponding image.

The first region 21 of the sensor 20 is continually interrogated at a very high rate in order to read out images 23 rapidly in succession. The read out frequency of the grey image region 24 is slower and is suited to the objective field and to the movement speed of the camera or the unit 9 relative to the join line 4.

With a data rate of the sensor of 80 MByte/sec and with a pixel count of 1K×1K the sensor region 21 can be read out with for example 150×800 pixels at about 660 hz. With a corresponding increase of the data rate to 160 Mbyte/sec a read out of about 1.2 KHz can be achieved.

A sensor region 22 with for example 800×800 pixels is so read out in dependence of the objective field and the process speed so that the images of the welding or joining bead 4 overlap one another.

Figure 3:
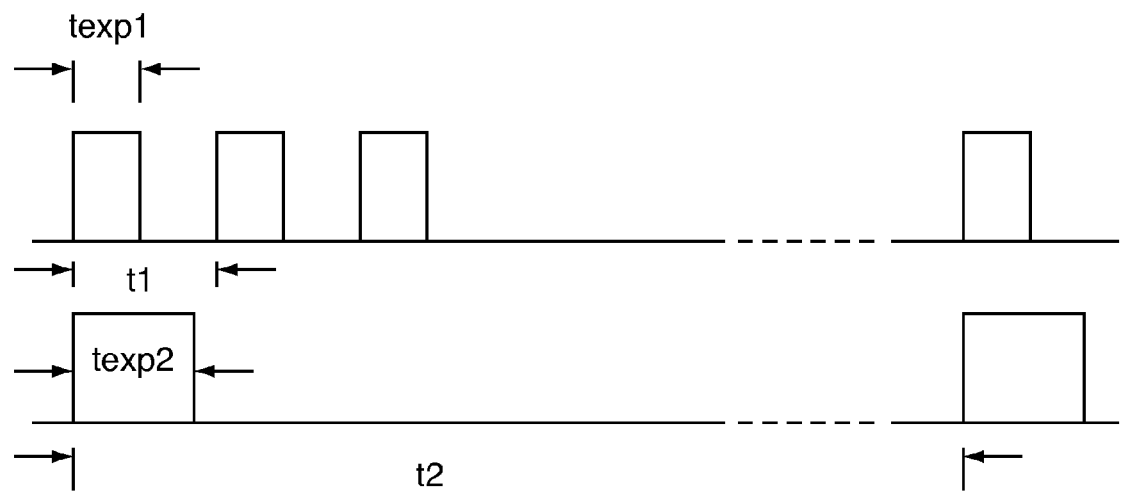
FIG. 3 a schematic representation of a sensor reading.

FIG. 3 shows schematically the read out of the two areas. The time texp1 is the exposure time for the sensor area 21, the time texp2 is the exposure time for the sensor area 22. The time t1 is the exposure time+the read out time for the sensor area 21, the time t2 is the exposure time+the read out time for the sensor area 22.

A sensor for the present method is obtainable from the firm Photonfocus AG, 8853 Lachen, Switzerland, and is marketed under the type designation MV-D 1024 CL.

With this sensor the read out can take place synchronously. In one embodiment of the invention this preferably occurs in that the data from the sensor is written into a memory 25 having memory areas 26 and 28, with the image data from the sensor region 21 reaching the memory area 26 and with the image date from the sensor region 22 reaching the memory area 28, as indicated by the broken lines in FIG. 4.

With synchronous type of operation therefore the sensor region 24 is continuously read out and after its capture the objective region for the sensor area 22 is read out.

Figure 4:
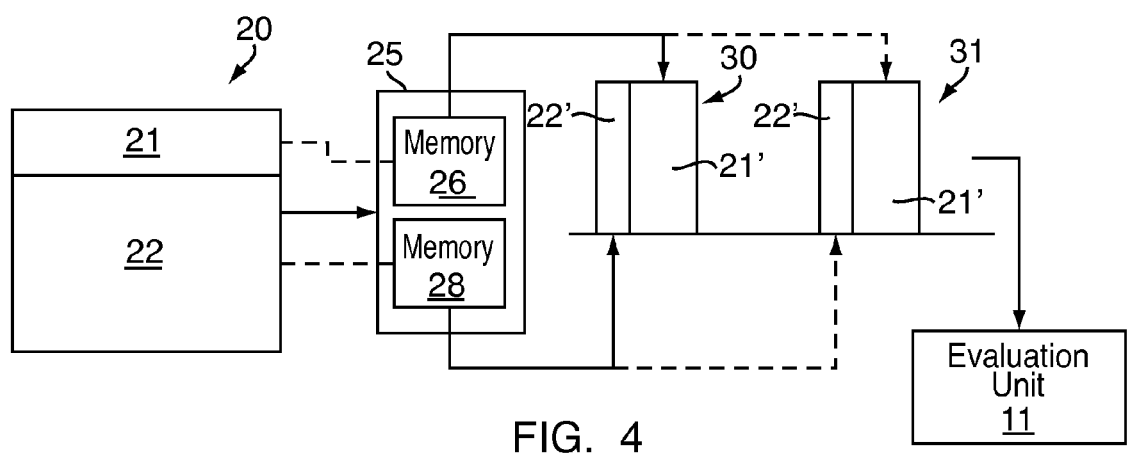
FIG. 4 a schematic representation of a sensor reading into a memory.

Since the transmission time for the sensor area 22 is substantially longer than that for the sensor region 21, the data for the sensor area 22 is intermediately stored and is then stepwise transmitted with the data of the sensor area 21, as indicated in FIG. 4. The data blocks 30, 31 . . . and so forth are therefore each formed from a complete image 21' of the triangulation line and a portion 22' of the image (partial amount of the sensor area 22) of the join line 4, and are passed on for evaluation (represented by the unit 11) where the individual triangulation line images are evaluated in rapid succession and the grey picture produced by a combination of the pieces 22' is evaluated, or the individual pieces 22' or several pieces 22' together are evaluated. The partial amount of the data must be so chosen that all the data of the sensor region 22 is transmitted within the time t2. The memory 26 can be arranged with the sensor in the unit 9 or in the camera or even in the unit 11.

Alternatively to the explained synchronous reading of the areas 21, 22 these regions can also be read asynchronously over separate channels, if permitted by the sensor 20. The images taken by the sensor are supplied to an image evaluation unit 11. Here the image for the evaluation unit 11 does not appear in visible form, but only as succession of numbers. It can be so carried out that in the unit 11 the data is processed with eight bit words. The separation of the grey value image can also take place using, for example, ten bit images from the sensor 20, and the data can subsequently be transmitted by way of corresponding tables (look-up tables) for example in the 8 bit region 0-200 (for the grey value image) and 200-255 (for the laser line).

The evaluation of each image then takes place for the laser line in a customary way, where by means of the laser line the transverse profile of the seam is obtainable. From this profile, in known ways, the geometric data of the seam, for example convexity, concavity and mutual edge displacement, are detectable. For these values there exist ISO-limit values, whose maintenance is so determined. The high value grey vaue image delivered by the unit 9 makes possible the determination of the welding quality by way of the evaluation of this image. For this in the image region which represents the seam 4 the contours of the seam structure are presented. This is known from WO 03/041902, the content of which is herewith incorporated by reference. Accordingly, the seam structure can be put into a dynamic binary form. In a further processing step, this dynamic binary seam data is skeletalized to leave, as a remainder, the contour lines of the seam structure.

For these processing steps corresponding image processing programs are known. The software SOUVIS5000 of the firm Soudronic Automotive AG, Switzerland can be used, and offers these functionalities. As a customary commercial further program, for example, a known program of the former firm Logical Vision, today Coreco Imaging, St. Laurent, Quebec, Canada, having the designation WiT can be used, for example in the version 5.3. The corresponding image processing permits the recognition of localized faults, for example porocities and small holes and failures of thorough welding. This on one hand can take place in that the so reported structures are compared with known patterns of good quality welding seams. Additionally or in place of this, because of the existence through the unit 11 of the contour lines, the orientation or the angular deflection from the seam longitudinal direction and/or their lengths can be tested. In this way it is now possible to examine the seam quality on the basis of a grey value image.

The invention in the preceding is explained in connection with a welding seam in the case of plate welding, but it is not limited to this use. It can in general examine the quality of join locations, for example in the case of spot welding or in the case of a bead of adhesive material.

The invention can also be used with the edge following unit 7. All of the details explained for the unit 9 can in this case be incorporated into or taken over by the unit 7. In this case especially the illumination and the image taking occur in a preferable way similar to that explained for the unit 9. The light line evaluation permits the edge recognition and the thickness jump supervision. The recognition of the edge with 0-depth/0-thickness jump and the measurement of the gap width occurs in advantageous ways through the grey scale image evaluation. Also in this case there exists by way of the preferred sensor implementation and the preferred type of illumination a qualitatively very good grey scale image with high resolution, large objective field, high dynamic range despite the high objective speed is made available. The unit 7 is here likewise connected by a conductor 12 with the image evaluator 11 as is the case with the conductor 14 for the unit 9. In this case according to the purpose of the unit 7 the laser source 5 is controlled by the unit 11 over the conductor 13 so that the welding by means of the laser beam occurs exactly at the position of the join line 3.

The unit 7 in this case can however be used, additionally to the position recognition, for the capturing of edge damages, to determine the quality of the join position in advance of the joining step, as has been explained in connection with the unit 9. If what is involved is the join position for an adhesive material bead, there results likewise the position and quality recognition by way of a unit corresponding to the unit 7 (or separately by way of two units) in advance of the joining step.

The purpose and the application field of the invention are: welding connections, laser as well as MIG and MAG connections must be submitted to 100% control. In the case of adhesive joining adhesive beads must be subjected a control. Coating weldings must be inspected before further processing.

High production speed capabilities connected with small fault limits lead to the use of optical measuring and testing systems which can test joins without contact at high speed.

In one such system fault recognition of the smallest local fault spots are expected in connection with a 3 dimensional measurement and include: 1. Recognition of local fault locations, measurement of seam length and positions; 2. Measurement of the geometric data such as convexity, concavity and perhaps edge thickness difference, in order to guarantee maintenance of the ISO limit values. Measurement of the seam volume, since an individual measured value such as for example of the concavity says nothing about the seam cross section.

A measurement of the geometric data demands a fast 3D measurement of the seam; the recognition of local fault spots requires a grey image evaluation with a high resolution and with concurrent rapid objective movement.

The resulting requirements for the image processing are: high resolution, large objective field, large dynamic range and high objective speed capability.

The recognition of local fault spots, which cannot be achieved with triangulation occurs in the foregoing by way of grey image analysis.

As to the weakness of the triangulation, a recognition of small local fault spots is made possible by the additional grey image evaluation in the sensor region 22. Both evaluations require only one sensor, which lowers considerably the expense for the apparatus, the expense for the operator and the expense for the maintenance, in comparison to a system having two sensors.

The space requirement and the associated costs are substantially lower than with the assembly of two sensors. Included in the application field is the recognition of welding edges for the guiding of the welding lasers, a quality supervision of welded seams of all kinds, a quality supervision of adhesive beads as well as the geometric supervision of outer surfaces with concurrent inspection of the outer surface quality.

The user can with the new sensor system carry out 3D measurement according to generally accepted light intersection methods at high frequency.

The supervision of local fault spots is carried out with the same system. The user need not install a further sensor system.

While in the present application preferred embodiments of the invention have been described it should be clearly understood that the invention is not limited to these and can be carried out in other ways within the embrace of the following claims.

The invention claimed is:

1. A method for the recognition of a join location of workpieces wherein by way of a light intersection method, lines of light are taken for capturing of a three dimensional course of the join location, and a grey value image of the join location is taken and evaluated for assessing the quality of the join location, and wherein the lines of light for the light intersection method and the grey value image are received by a sensor, characterized in that the taking of said lines of light is taken in a first region of the sensor and the reception of the grey value image is taken in a further second region of the sensor separate from the first region, which sensor regions are time-wise differently exposed and which sensor regions are time-wise differently interrogated.

2. A method according to claim 1 further characterized in that the two regions of the sensor are interrogated independently and asynchronously from one another.

3. A method accordingly to claim 1, further characterized in that the two regions of the sensor are synchronously interrogated and the results are stored intermediately in a memory from which data blocks each containing a complete line of light image and a portion of the grey value image are taken.

4. A method according to claim 1, further characterized in that with relative movement between workpieces and the sensor, the exposure time for at least one line of light is chosen to be so long that the light of the line is reflected from an area of the seam which is broader than the light line.

5. A method according to claim 1 further characterized in that with relative movement between the workpieces and the sensor, the exposure time for the grey value image taken by means of a flash illuminating apparatus is chosen to be so short that the movement severity is held to be smaller than one pixel.

6. A method according to claim 1 further characterized in that instead of a grey value image or in addition to the grey value image a color image is taken.

7. A method according to claim 1 for further assessing of edge faults in the case of plate welding.

8. A method according to claim 1 for further assessing of welding seam quality in the case of plate welding.

9. A method according to claim 8, further characterized in that contours of the structure of the welding seam are produced and investigated.

10. A method according to claim 1, for further assessing of spot weldings or adhesive beads.

11. A method according to claim 1 wherein the sensor is a CMOS-sensor.

12. A device for the recognition of join locations of workpieces with a light line projecting unit and a photographing unit for the photographing of the light line and a grey value image, as well as with an image evaluation unit for the light line and the grey value image, which evaluation unit is equipped for the recognition of quality features of the joint position by way of a grey value image evaluation, wherein the photographing unit is constructed for the taking of one image which contains both the light line and the grey value image, and wherein the photographing unit has a sensor, characterized in that a photograph of the at least one light line is taken in a first area of the sensor and the photograph of the grey value image is taken in a second area of the sensor different from the first area, which areas are time-wise differently exposed and which areas of the sensors are time-wise differently interrogated.

13. A device according to claim 12 further characterized in that the two areas of the sensor are interrogated independently and asynchronously from one another.

14. A device according to claim 12 further characterized in that the two areas of the sensor are interrogated synchronously and are stored temporarily in a memory from which memory are taken data blocks each containing a complete light line image and a portion of the grey value image.

15. A device according to claim 12 further characterized in that a flash illuminating unit is provided for the taking of the grey value image.

16. A device according to claim 12 further characterized in that the image evaluation unit is equipped for obtaining and assessing of contours of the region of the join location in the grey value image.

17. A device according to claim 12, further characterized in that the photographing unit is equipped for taking an additional colored image or for taking a color image in place of the grey value image.

18. A device according to claim 12 wherein the sensor is the only sensor of the photograph unit.

19. A device according to claim 12 wherein the sensor is a single CMOS-sensor.

* * * * *